United States Patent
Lawson

(10) Patent No.: US 8,987,293 B2
(45) Date of Patent: Mar. 24, 2015

(54) MORPHINANS USEFUL AS ANALGESICS

(75) Inventor: John Lawson, Hyde Park, UT (US)

(73) Assignee: Phoenix Pharmalabs, Inc., Providence, UT (US)

( * ) Notice: Subject to any disclaimer, the term of this patent is extended or adjusted under 35 U.S.C. 154(b) by 0 days.

(21) Appl. No.: 13/981,160

(22) PCT Filed: Dec. 23, 2011

(86) PCT No.: PCT/US2011/067116
§ 371 (c)(1),
(2), (4) Date: Sep. 3, 2013

(87) PCT Pub. No.: WO2012/088494
PCT Pub. Date: Jun. 28, 2012

(65) Prior Publication Data
US 2013/0338182 A1    Dec. 19, 2013

Related U.S. Application Data

(60) Provisional application No. 61/426,727, filed on Dec. 23, 2010.

(51) Int. Cl.
*C07D 221/28* (2006.01)
*C07D 221/22* (2006.01)

(52) U.S. Cl.
CPC .......... *C07D 221/28* (2013.01); *C07D 221/22* (2013.01)
USPC ............................................ 514/289; 546/74

(58) Field of Classification Search
None
See application file for complete search history.

(56) References Cited

U.S. PATENT DOCUMENTS

| 4,218,454 | A | 8/1980 | DeGraw et al. |
| 4,269,843 | A | 5/1981 | DeGraw et al. |
| 4,567,183 | A * | 1/1986 | Sunshine et al. ......... 514/263.31 |
| 7,629,355 | B2 | 12/2009 | Lawson |
| 2003/0073716 | A1 | 4/2003 | Neumeyer et al. |
| 2005/0191340 | A1 | 9/2005 | Bartholomaeus et al. |
| 2009/0318699 | A1 | 12/2009 | Lawson |

FOREIGN PATENT DOCUMENTS

WO    9531464 A1    11/1995

OTHER PUBLICATIONS

Khroyan et al. "SR 16435 [1-1(-(Bicyclo[3.3.1]nonan-9-yl)piperidin-4-yl)indolin-2-one], a Novel Mixed Nociceptin/Orphanin FQ/ μ-Opioid Receptor Partial Agonist: Analgesic and Rewarding Properties in Mice" The Journal of Pharmacology and Experimental Therapeutics, vol. 320; No. 2; 934-943; (2007).
International Search Report of the International Searching Authority for International Application No. PCT/US2011/067116; International Filing Date: Dec. 23, 2011; 6 Pages.
Written Opinion of the International Searching Authority for International Application No: PCT/US2011/067116; International Filing Date: Dec. 23, 2011; 4 Pages.
Toll et al., "Standard Binding and Functional Assays Related to Medications Development Division Testing for Potential Cocaine and Opiate Narcotic Treatment Medications" NIDA Res. Monograph 178, The College on Problems of Drug Dependence, 59th Annual Meeting, pp. 440-466. (1998).
Toll et al., "Comparison of the Antinociceptive and Antirewarding Profiles of Novel Bifunctional Nociceptin Receptor/μ-Opioid Receptor Ligands: Implications for Thereapeutic Applications" The Journal of Pharmacology and Experimental Therapeutics, vol. 331; No. 3; 954-64 (2009).
Traynor et al., "Modulation by μ-Opioid Agonists of Guanosine-5'-O-(3-[35S]thio)triphosphate Binding to Membranes from Human Neuroblastoma SH-Sy5Y Cells" Molecular Pharmacology; vol. 47 pp. 848-854, (1995).

\* cited by examiner

*Primary Examiner* — Janet L Andres
*Assistant Examiner* — Timothy R Rozof
(74) *Attorney, Agent, or Firm* — Cantor Colburn LLP

(57) ABSTRACT

Compounds of Formula (I) are disclosed.

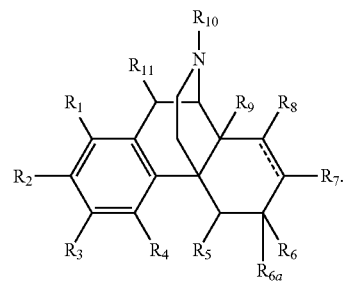

Formula (I)

The variables $R_1$-$R_{11}$ are described herein. Certain compounds of Formula (I) are partial agonists of the mu, delta, and kappa opioid receptors, and are useful for treating pain and opioid addiction, with fewer side effects than conventional opioids. Methods for preparing the disclosed compounds, pharmaceutical compositions containing compounds of Formula (I), and methods of treating pain and opioid addiction in patients are also disclosed.

9 Claims, No Drawings

MORPHINANS USEFUL AS ANALGESICS

CROSS REFERENCE TO RELATED APPLICATION

This application is a national stage application of PCT/US2011/067116, filed Dec. 23, 2011, which claims priority from U.S. Provisional Appl. No. 61/426,727, filed Dec. 23, 2010, which is hereby incorporated by reference in its entirety.

FIELD OF THE DISCLOSURE

Novel morphinans of Formula (I) are disclosed. Certain compounds disclosed herein partial agonists of the mu, delta, and kappa opioid receptors, and are useful for treating pain and opioid addiction. Methods for preparing the disclosed compounds are also provided. Pharmaceutical compositions containing the novel morphinans of Formula (I) are disclosed, as are methods of treating patients who are experiencing pain or opioid dependency.

BACKGROUND

Pain is a complex and poorly understood bodily response and a major health problem that often confers a low quality of life. In clinical practice, an "ideal" analgesic should: (a) reduce pain with high efficacy; (b) provide convenient dosing and predictable serum concentrations; and (c) exert minimal side effects and abuse liability. Current analgesics possess one or two of these properties, but none of them relieves pain completely and/or without side effects or addiction issues.

Opioids are the oldest and most prescribed analgesics, primarily as a first-line choice for acute and chronic surgical, cancer, and back pain. Opioids are divided into two primary classes: (a) "mu-active" drugs (e.g., morphine), which are selective for the mu-opioid receptor, and (b) "mixed agonist/antagonist" drugs (e.g., butorphanol, nalbuphine), which typically recognize mu- and kappa-opioid receptors. While opioids are effective in their primary indications, they elicit many limiting side effects, including constipation, respiratory and cardiovascular depression, nausea, urinary retention/diuresis, sedation, dysphoria, tolerance, and/or physical dependence, which seem virtually inseparable from their analgesic effects. Due to such problems, pain patients sometimes take less than the prescribed dosage and/or endure pain rather than suffer from side effects. Such problems also plague physicians, who must monitor patients closely, rotate different drugs to determine the most tolerable drug and dosage, and/or administer extra medicines to counteract side effects.

Morphinans are compounds based on the core chemical structure

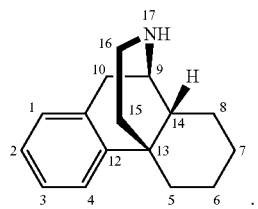

Morphine, a widely used and powerful analgesic, is a common example of a morphinan. Morphine is an opioid that binds to opioid receptors in the central nervous system. However, the drug has serious side effects that present severe clinical problems, including drug dependence, suppression of respiration and suppression of smooth muscle movement. Alternative morphinan analogs have been studied and investigated in a search for compounds that shares the benefits of morphine with fewer negative side effects.

Due to the side effects and chemical dependency liability of currently available analgesics, there here nonetheless remains a need for additional opioid analgesics. Effective, non-addicting analgesics are particularly needed. The novel morphinan compounds of Formula I disclosed herein fulfill this need and provide additional advantages that are discussed in this disclosure.

SUMMARY

Applicants have discovered novel morphinans and related compounds. Certain of these compounds possess unique combinations of high binding affinities and partial agonist activities at mu, delta, and kappa opioid receptors. These compounds are included in Formula (I) below and other subformula of Formula (I) disclosed herein. In vivo, preferred compounds of Formula (I) elicit potent analgesia with few side effects and no apparent addiction liability. Certain compounds of Formula (I) are also useful for treating opioid addiction.

Compounds of Formula (I) and their pharmaceutically acceptable salts are disclosed in this document.

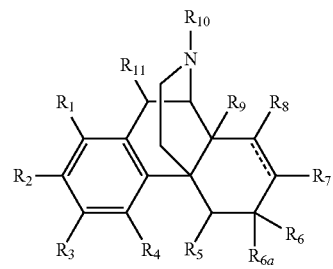

Formula (I)

The dashed line between $R_7$ and $R_8$ in Formula I represents an optional double bond.

The variables $R_1$, $R_2$, $R_3$, $R_4$, $R_5$, $R_6$, $R_{6a}$, $R_7$, $R_8$, $R_9$, $R_{10}$ and $R_{11}$ have the definitions given below and the definition of each variable is independent of the definition of any of the other variables.

$R_1$, $R_2$, $R_3$, $R_4$, $R_5$, $R_6$, $R_{6a}$, $R_7$, $R_8$, $R_9$, $R_{10}$ and $R_{11}$ are independently selected from (i) hydrogen, hydroxyl, amino, cyano, and halogen; and
(ii) hydrocarbyl and heteroatom-containing hydrocarbyl, each of which (ii) is unsubstituted or substituted.

$R_{10}$ is hydrocarbyl or a carbon-linked heteroatom-containing hydrocarbyl, each of which is unsubstituted or substituted.

Pharmaceutical compositions comprising a compound or salt of Formula I or any subformula of Formula I, together with a pharmaceutically acceptable carrier, are also provided.

Methods of treating pain or opioid addiction comprising administering an effective amount of a compound or salt of Formula I or any subformula of Formula (I) to a patient in need of such treatment are provided. Methods for preparing a compound of Formula (I), comprising isolating one diastereomer from a mixture of diastereomers, where the mixture of diastereomers is prepared by demethylating levorphanol and N-alkylating the demethylated product is provided herein.

DETAILED DESCRIPTION

Terminology

Before describing the invention in detail, it will be helpful to have these definitions of terms used in the claims and elsewhere in the specification. Compounds are described using standard nomenclature.

Unless otherwise indicated, the disclosure is not limited to specific procedures, starting materials, or the like, as such may vary. It is also to be understood that the terminology used herein is for the purpose of describing particular embodiments only and is not intended to be limiting. Unless clearly contraindicated by the context each compound name includes the free acid or free base form of the compound as well as hydrates and pharmaceutically acceptable salts of the compound.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). The open ended term "comprising" encompasses the terms "consisting of" and "consisting essentially of."

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

In describing and claiming the present invention, the following terminology will be used in accordance with the definitions set out below.

The phrases "for example," "for instance," "such as," or "including" are meant to introduce examples that further clarify more general subject matter. These examples are provided only as an aid for understanding the disclosure, and are not meant to be limiting in any fashion.

The terms "optional" and "optionally," mean that the subsequently described circumstance may or may not occur, so that the description includes instances where the circumstance occurs and instances where it does not. For example, the phrase "optionally substituted" means that a non-hydrogen substituent may be present on a given atom, and, thus, the description includes structures wherein a non-hydrogen substituent is present and structures wherein a non-hydrogen substituent is not present.

The term "independently selected from" is used herein to indicate that the recited elements, e.g., R groups or the like, can be identical or different.

"Alkyl" is a branched or unbranched saturated hydrocarbon group generally containing 1 to about 12 carbon atoms, such as methyl, ethyl, n-propyl, isopropyl, n-butyl, isobutyl, t-butyl, octyl, decyl, or the specified number of carbon atoms. Other embodiments include alkyl groups having from 1 to 8 carbon atoms, 1 to 4 carbon atoms or from 1 to 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, (cycloalkyl)$C_0$-$C_4$ alkyl, the indicated group, in this case cycloalkyl, is either directly bound by a single covalent bond ($C_0$), or attached by an alkyl chain having the specified number of carbon atoms, in this case from 1 to about 4 carbon atoms.

"Alkenyl" is a straight or branched hydrocarbon chain comprising one or more unsaturated carbon-carbon double bonds, which may occur in any stable point along the chain. Alkenyl groups described herein have the indicated number of carbon atoms. E.g. $C_2$-$C_6$alkenyl indicates an alkenyl group of from 2 to about 6 carbon atoms. When no number of carbon atoms is indicated, alkenyl groups described herein typically have from 2 to about 12 carbon atoms, though lower alkenyl groups, having 8 or fewer carbon atoms, are preferred. Examples of alkenyl groups include ethenyl, propenyl, and butenyl groups.

"Alkoxy" is an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. When "$C_0$-$C_n$alkoxy" is used in conjunction with another group, for example, (cycloalkyl)$C_0$-$C_4$ alkoxy, the indicated group, in this case cycloalkyl, is either attached via a covalently bound oxygen bridge ($C_0$alkoxy), or attached by an alkoxy group having the specified number of carbon atoms, in this case from 1 to about 4 carbon atoms, that is covalently bound to the group it substitutes via the alkoxy oxygen atom. Likewise when the suffix "oxy" used in conjunction with another group, for example "alkenyloxy" the first term, in this case alkenyl, has the definition given in this section, and oxy indicates the first group is attached to the atom it substitutes through an oxygen bridge (—O—).

"Halo" and "halogen" mean a chloro, bromo, fluoro or iodo substituent.

"Hydrocarbyl" groups are univalent hydrocarbon radicals, which are saturated or unsaturated, may be linear, branched, or cyclic, and typically containing 1 to about 12 carbon atoms, 1 to about 8 carbon atoms, or 1 to about 6 carbon atoms, or the specified number of carbon atoms. Examples of hydrocarbyl groups include alkyl groups, alkenyl groups, aryl groups, cycloalkyl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with an atom other than carbon (heteroatom), e.g., nitrogen, oxygen, sulfur, phosphorus or silicon, typically nitrogen, oxygen or sulfur.

The term "heteroatom-containing" as in a "heteroatom-containing alkyl group" refers to a molecule, linkage or substituent in which one or more carbon atoms is replaced with an atom other than carbon, e.g., nitrogen, oxygen, sulfur, phosphorus or silicon, typically nitrogen, oxygen or sulfur.

"Levorphanol" is a morphinan opioid of the structure

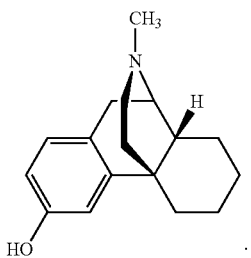

"Oxo," is a keto group (C=O). An oxo group that is a substituent of a nonaromatic carbon atom results in a conversion of —CH$_2$— to —C(=O)—. An oxo group that is a substituent of an aromatic carbon atom results in a conversion of —CH— to —C(=O)— and a loss of aromaticity.

By "substituted" as in "substituted hydrocarbyl," and the like, as alluded to in some of the aforementioned definitions, is meant that in the hydrocarbyl or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated. Preferred substituents include halogen, hydroxyl, amino, cyano, oxo, —CHO, —COOH, $C_1$-$C_6$alkyl, $C_2$-$C_6$alkanoyl, $C_2$-$C_6$alkenyl, $C_2$-$C_6$alkynyl, ($C_3$-$C_7$cycloalkyl)$C_0$-$C_2$alkyl, (heterocycloalkyl)$C_0$-$C_2$alkyl, $C_1$-$C_6$alkylthio, $C_1$-$C_6$alkylester, mono- and di-$C_1$-$C_6$alkylamino, $C_1$-$C_6$haloalkyl, $C_1$-$C_6$haloalkoxy, mono- and di-$C_1$-$C_6$alkylcarboxamide, mono- and di-$C_1$-$C_6$alkylsulfonamide, and phenyl.

The term "enantioenriched" is used to indicate that, where a compound may exist as two or more enantiomers, one of the enantiomers is present in excess of the other(s). For example, where two enantiomers of a compound are possible, an enantioenriched sample may include greater than 50%, greater than 60%, greater than 70%, greater than 75%, greater than 80%, greater than 85%, greater than 90%, greater than 95%, or greater than 99% of one of the enantiomers. A process is "enantioenriching" or "enantioselective" when the process favors production of one enantiomer over production of another enantiomer. Similarly, the term "diastereomerically enriched" is used to indicate that, where a compound may exist as two or more diastereomers, one of the diastereomers is present in excess of the other(s). For example, where two diastereomers of a compound are possible, a diastereomerically enriched sample may include greater than 50%, greater than 60%, greater than 70%, greater than 75%, greater than 80%, greater than 85%, greater than 90%, greater than 95%, or greater than 99% of one of the diastereomers. A process is "diastereomerically enriching" or "diastereoselective" when the process favors production of one diastereomer over production of another diasteomer.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

"Pharmaceutical compositions" are compositions comprising at least one active agent, such as a compound or salt of Formula (I), and at least one other substance, such as a carrier, excipient, or diluent. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like.

The term "carrier" applied to pharmaceutical compositions of the invention refers to a diluent, excipient, or vehicle with which an active compound is provided.

"Providing" means giving, administering, selling, distributing, transferring (for profit or not), manufacturing, compounding, or dispensing.

"Providing a compound of Formula (I) with at least one additional active agent" means the compound of Formula (I) and the additional active agent(s) are provided simultaneously in a single dosage form, provided concomitantly in separate dosage forms, or provided in separate dosage forms for administration separated by some amount of time that is within the time in which both the compound of Formula (I) and the at least one additional active agent are within the blood stream of a patient. The compound of Formula (I) and the additional active agent need not be prescribed for a patient by the same medical care worker. The additional active agent or agents need not require a prescription. Administration of the compound of Formula (I) or the at least one additional active agent can occur via any appropriate route, for example, oral tablets, oral capsules, oral liquids, inhalation, injection, suppositories or topical contact.

"Treatment," as used herein includes (a) providing a compound of Formula (I) prophylactically to prevent pain in a patient, e.g. preoperative administration of a compound of Formula (I) to prevent surgical pain (b) inhibiting a condition, i.e. arresting its development; and (c) relieving the condition, i.e., causing regression of pain.

A "therapeutically effective amount" of a pharmaceutical combination of this invention means an amount effective, when administered to a patient, to provide a therapeutic benefit such as an amelioration of symptoms, e.g., an amount effective to decrease pain.

Chemical Description

Compounds and pharmaceutically acceptable salts of Formula (I) are disclosed.

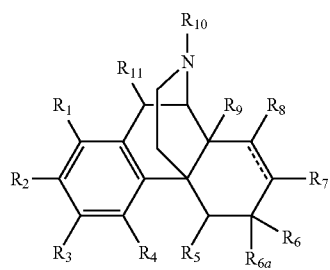

Formula (I)

In Formula (I) the variables, e.g. $R_1$, $R_2$, $R_3$, $R_5$, $R_5$, $R_6$, $R_{6a}$, $R_7$, $R_8$, $R_9$ $R_{10}$ and $R_{11}$ may have the definitions listed in the "Summary" section or may have any of the definitions listed in this section. Any combination of variable definitions is within the scope of this disclosure so long as a stable compound results.

Compounds of Formula (Ia)-Formula (If), which are sub-formulae of Formula (I), are also provided.

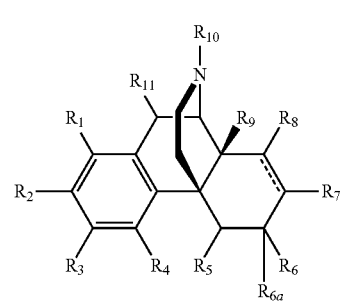

Formula (Ia)

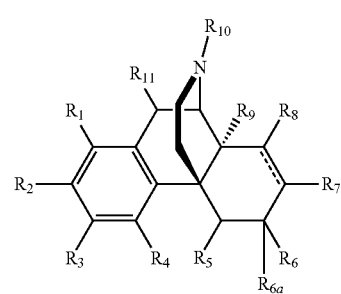

Formula (Ib)

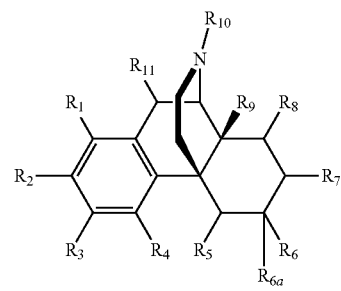

Formula I(c)

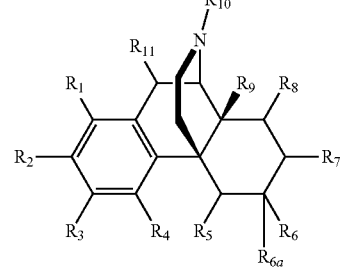

Formula I(d)

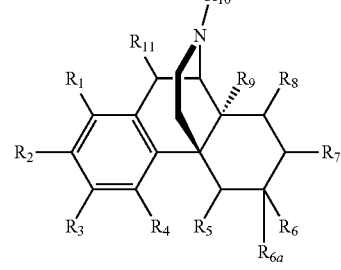

Formula I(e)

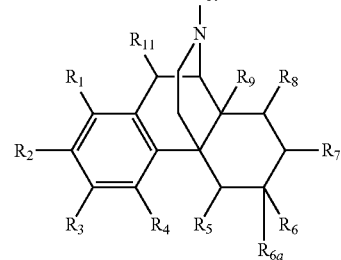

Formula I(f)

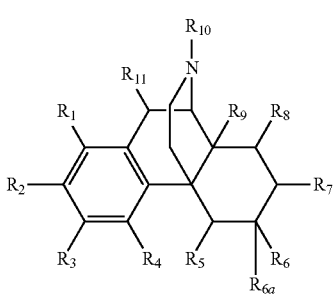

In one embodiment $R_1$, $R_2$, $R_3$, $R_4$, $R_5$, $R_6$, $R_{6a}$, $R_7$, $R_8$, $R_9$, and $R_{11}$ are independently selected from (i) hydrogen, hydroxyl, cyano, and halogen; and (ii) hydrocarbyl and heteroatom-containing hydrocarbyl, each of which (ii) is unsubstituted or substituted with one or more substituents independently chosen from hydroxyl, amino, cyano, halogen, oxo, —COOH, —CONR$_{11}$R$_{12}$, —SO$_2$NR$_{11}$R$_{12}$, and —NR$_{11}$COR$_{12}$, where R$_{11}$ and R$_{12}$ are independently chosen from hydrogen and $C_1$-$C_6$alkyl.

$R_{10}$ is hydrocarbyl or carbon-linked heteroatom-containing hydrocarbyl, unsubstituted or substituted with one or more substituents independently chosen from hydroxyl, amino, cyano, halogen, oxo, —COOH, —CONR$_{11}$R$_{12}$, —SO$_2$NR$_{11}$R$_{12}$, and —NR$_{11}$COR$_{12}$, where R$_{11}$ and R$_{12}$ are independently chosen from hydrogen and $C_1$-$C_6$alkyl.

This disclosure includes the following embodiments:

(A) $R_1$, $R_2$, $R_4$, $R_5$, $R_6$, $R_{6a}$, $R_7$, $R_8$, $R_9$, and $R_{11}$ are independently selected from (i) hydrogen, hydroxyl, cyano, and halogen; and (ii) $C_1$-$C_8$alkyl, $C_2$-$C_8$alkenyl, and ($C_3$-$C_7$cycloalkyl)$C_0$-$C_4$alkyl, each containing zero or one or two heteroatoms independently chosen from N, O, and S, each of which (ii) is unsubstituted or substituted with one or more substituents independently chosen from hydroxyl, amino, cyano, halogen, oxo, —COOH, —CONR$_{11}$R$_{12}$, —SO$_2$NR$_{11}$R$_{12}$, and —NR$_{11}$COR$_{12}$, where R$_{11}$ and R$_{12}$ are independently chosen from hydrogen and $C_1$-$C_6$alkyl.

$R_3$ is (i) hydroxyl, halogen, or (ii) $C_1$-$C_8$alkoxy, $C_2$-$C_8$alkenyloxy, and ($C_3$-$C_7$cycloalkyl)$C_0$-$C_4$alkoxy, each containing zero or one or two heteroatoms independently chosen from N, O, and S, each of which (ii) is unsubstituted or substituted with one or more substituents independently chosen from hydroxyl, amino, cyano, halogen, oxo, —COOH, —CONR$_{11}$R$_{12}$, —SO$_2$NR$_{11}$R$_{12}$, and —NR$_{11}$COR$_{12}$, where R$_{11}$ and R$_{12}$ are independently hydrogen and $C_1$-$C_6$alkyl.

$R_{10}$ is $C_1$-$C_8$alkyl, $C_2$-$C_8$alkenyl, and ($C_3$-$C_7$cycloalkyl)$C_0$-$C_4$alkyl, each attached to the $R_{10}$ position via a carbon-carbon bond, and containing zero or one or two heteroatoms independently chosen from N, O, and S, each of which (ii) is unsubstituted or substituted with one or more substituents independently chosen from hydroxyl, amino, cyano, halogen, oxo, —COOH, —CONR$_{11}$R$_{12}$, —SO$_2$NR$_{11}$R$_{12}$, and —NR$_{11}$COR$_{12}$, where R$_{11}$ and R$_{12}$ are independently chosen from hydrogen and $C_1$-$C_6$alkyl.

(B) $R_1$, $R_2$, $R_3$, $R_4$, $R_5$, $R_6$, $R_{6a}$, $R_7$, $R_8$, $R_9$, and $R_{11}$ are independently selected from: hydrogen, halogen, hydroxyl, amino, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy; and $R_3$ is hydroxyl, halogen, or $C_1$-$C_4$alkoxy.

(C) $R_1$, $R_2$, $R_3$, $R_4$, $R_5$, $R_6$, $R_{6a}$, $R_7$, $R_8$, $R_9$, and $R_{11}$ are independently selected from: hydrogen, halogen, $C_1$-$C_2$alkyl, and $C_1$-$C_2$alkoxy.

(D) $R_1$, $R_2$, $R_4$, $R_5$, $R_7$, $R_8$, $R_9$, and $R_{11}$ are independently selected from: hydrogen, halogen, hydroxyl, amino, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy;

$R_3$ is hydroxyl, halogen, or $C_1$-$C_4$alkoxy;

$R_6$ is hydroxyl, halogen, or $C_1$-$C_4$alkoxy; and $R_{6a}$ is hydrogen, halogen, $C_1$-$C_4$alkyl, or $C_1$-$C_4$alkoxy.

(E) $R_3$ is hydroxyl.

(F) $R_1$, $R_2$, $R_4$, $R_5$, $R_{6a}$, $R_7$, $R_8$, $R_9$, and $R_{11}$ are all hydrogen; $R_3$ is hydroxyl; and $R_6$ is hydrogen or hydroxyl.

(G) $R_{10}$ is $C_1$-$C_8$alkyl, $C_2$-$C_8$alkenyl, or ($C_3$-$C_7$cycloalkyl)$C_0$-$C_4$alkyl, each of which is unsubstituted or substituted with one or more substituents independently chosen from hydroxyl, amino, cyano, halogen, oxo, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

(H) $R_{10}$ is $C_2$-$C_6$alkyl, $C_2$-$C_6$alkenyl, or (cyclopropyl)$C_1$-$C_4$alkyl.

(I) $R_3$ is —OR$_a$, where $R_a$ is hydrogen, alkyl, aryl, arylalkyl, alkylaryl or a hydroxyl protecting group, or $R_3$ is —N(R$_b$)(R$_c$) where R$_b$ and R$_c$ are selected from alkyl, alkanoyl, and aryl and amine protecting groups where $R_a$ is hydrogen, alkyl, aryl, arylalkyl, alkylaryl or a hydroxyl protecting group.

(J) $R_{10}'$ is (R$_{12}$)(R$_{13}$) where R$_{12}$ and R$_{13}$ may be the same or different and are selected from $C_1$-$C_{12}$alkyl, heteroatom-containing $C_1$-$C_{12}$ alkyl, and substituted heteroatom-containing $C_1$-$C_{12}$alkyl.

In yet another embodiment this disclosure provides a compound or pharmaceutically acceptable salt thereof of Formula (II) (which is a subformula of Formula (I)).

Formula (II)

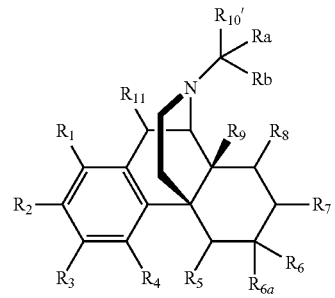

Within Formula (II) the variables have the following definitions:

$R_1$, $R_2$, $R_4$, $R_5$, $R_6$, $R_{6a}$, $R_7$, $R_8$, $R_9$, and $R_{11}$ are independently selected from: hydrogen, halogen, hydroxyl, amino, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy; and $R_3$ is hydroxyl or $C_1$-$C_4$alkoxy.

$R_{10}'$ is hydrogen, halogen, hydroxyl, amino, $C_1$-$C_4$alkyl, $C_1$-$C_4$alkoxy, mono- or di-$C_1$-$C_4$alkylamino, $C_1$-$C_2$haloalkyl, or $C_1$-$C_2$haloalkoxy; and $R_a$ and $R_b$ are independently hydrogen, halogen, methyl, or ethyl.

This disclosure also provides a compound or pharmaceutically acceptable salt thereof of Formula (III) (which is a subformula of Formula (I)).

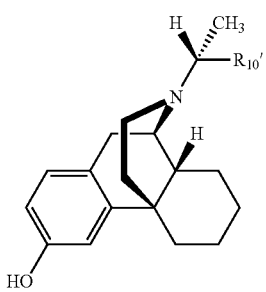

In Formula III, $R_{10}'$ includes cyclopropyl, ethyl, propyl, or vinyl.

Also included are the following specific embodiments:

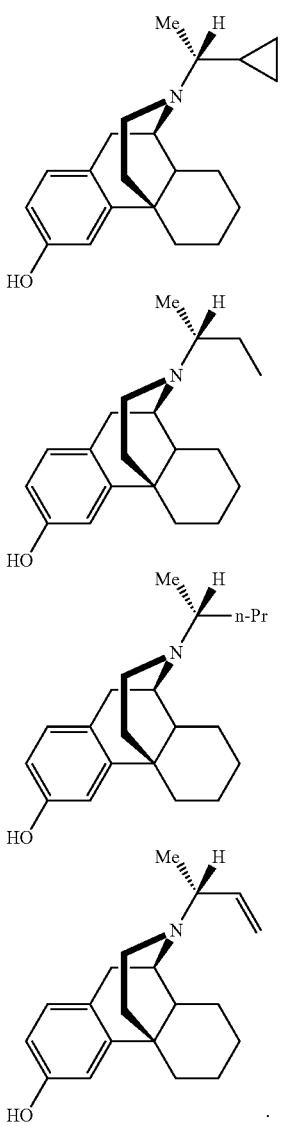

Pharmaceutical Preparations

Compounds of Formula (I) can be administered as the neat chemical, but are preferably administered as a pharmaceutical composition. Accordingly, the disclosure provides pharmaceutical compositions comprising a compound or pharmaceutically acceptable salt of the Formula (I), together with at least one pharmaceutically acceptable carrier. The pharmaceutical composition may contain a compound or salt of Formula (I) as the only active agent, or may contain one or more additional active agents.

Compounds of Formula (I) may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions can be formulated for oral administration. These compositions contain between 0.1 and 99 weight % (wt. %) of a compound of Formula (I) and usually at least about 5 wt. % of a compound of Formula (I). Some embodiments contain from about 25 wt. % to about 50 wt. % or from about 5 wt. % to about 75 wt. % of the compound of Formula (I).

Methods of Use

This disclosure includes methods of treating and preventing pain (prophylactic treatment) and treating opioid addiction by providing an effective amount of Formula (I) to a patient in need of such treatment. The patient may be a non-human animal such as a livestock animal or companion animal (e.g. cats, dogs) or a human patient. Prophylactic treatment includes administering a compound of Formula (I) just prior to a painful event such as surgery, bone-setting, or dental treatment.

In certain embodiments the compound of Formula (I) is a partial agonist at each of the mu-, kappa-, and delta-opioid receptors and has a high or medium affinity toward each of the mu-, kappa-, and delta-opioid receptors. In certain embodiment the compound of Formula (I) has a binding affinity (Ki) of less than 10.0 nM at each of the mu-, kappa-, and delta-opioid receptors and/or and $EC_{50}$ value of less than 30 nM at each of the mu-, kappa-, and delta-opioid receptors. In certain embodiment the compound of Formula I is administered as a single diasteromer or as a diastereomerically enriched mixture of diastereomers. Certain compounds of Formula (I) exhibit increased delta opioid receptor affinity. Such compounds may suppress drug tolerance, avert the conditioned rewarding affect associated with many opioids, and block physical dependence on opioids. Certain compounds exhibit a delta opioid receptor affinity that is not more than 20 fold less, not more than 10 fold less, not more than 5 fold less than the compound's mu opioid receptor affinity.

The compounds of Formula (I) may be used to treat are variety of painful conditions, including nociceptive pain, caused by tissue damage and the resultant stimulation of specific pain receptors, and non-nociceptive pain, which is caused by nerve damage or dysfunction. Non-nociceptive pain is also called neuropathic pain. Compounds of Formula (I) are particularly useful for treating nociceptive pain, but may also be used to treat certain types of neuropathic pain. Most opioids are not effective for treating neuropathic pain. Without wishing to be bound to any particular theory, we understand compounds of Formula (I) to be surprisingly effective for treating neuropathic pain due to their activity at the kappa receptor. Types of pain that can be treated with compounds of Formula (I) further include somatic pain, inflammatory pain, ischaemic muscle cramps, visceral pain, nerve pain (e.g. pain due to pinched nerve or trapped nerve), abdominal pain, pain due to nerve inflammation (e.g. torn or slipped disc), pain due to nerve infection (e.g. shingles also called postherpetic zoster pain), pain due to nerve degeneration (e.g. stroke, multiple sclerosis, brain haemorrhage), and sciatica. Other types of pain that can be treated with compound of Formula (I) include thalamic pain syndrome, burn pain, pain due to external nerve compression (e.g. tumor nerve compression), trigeminal neuralgia, dysmenorrheal cramps, pain due to endometriosis, and hyperalgesia.

Compounds and salts of Formula (I) are also useful for treatment of opioid addiction. In one embodiment an opioid addicted patient is provided a daily oral dose of a compound of Formula (I). The opioid content of the addicted patient's urine may be analyzed to determine treatment efficacy, where decreased frequency of urine samples positive for opioids indicates effective treatment, though preferably an effectively treated patient will consistently have urine samples negative for opioids. Effective treatment of opioid addicted patients with a compound of Formula (I) also comprises administering an amount of a compound of Formula (I) sufficient to suppress cumulative withdrawal symptoms when substituted for an opioid to which the patient is addicted.

The disclosure provides a method of eliciting analgesia in a human patient, while producing less reduced side effects compared with those typically exhibited by morphine.

Methods of treatment include providing certain dosage amounts of a compound of Formula (I) to a patient. Dosage levels of Formula (I) of from about 0.01 mg to about 140 mg per kilogram of body weight per day are useful in the treatment of the above-indicated conditions (about 0.5 mg to about 7 g per patient per day). In certain embodiments 1 mg to 500 mg, or 25 mg to 200 mg of a compound of Formula (I) are provided daily to a patient.

Frequency of dosage may also vary depending on the compound used and the particular disease treated. However, for treatment of most painful disorders, a dosage regimen of 4 times daily or less is preferred, and a dosage regimen of 1 or 2 times daily is particularly preferred. For treatment of opioid addition a dosage regimen of 1 times daily or less particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disorder for the patient undergoing therapy.

Compound of Formula (I) may be used alone or in combination with another active agent. The other active agent may be, for example, an opioid, cannabinoid, antidepressant, muscle relaxant, anticonvulsants, neuroleptics, antihistamines, acetaminophen, corticosteroids, ion channel blocking agents, non-steroidal anti-inflammatory drugs (NSAIDs), or diuretics.

Suitable does for a compound of Formula (I) when used in combination with a second active agent are generally as described above. Doses and methods of administration of other therapeutic agents can be found, for example, in the manufacturer's instructions in the Physician's Desk Reference. In certain embodiments, the combination administration of a compound of Formula (I) with the second active agent results in a reduction of the dosage of the second active agent required to produce a therapeutic effect (i.e., a decrease in the minimum therapeutically effective amount). Thus, preferably, the dosage of second active agent in a combination or combination treatment method is less than the maximum dose advised by the manufacturer for administration of the second active agent without combination administration of a compound of Formula (I). In certain embodiment this dosage is less than ¾, less than ½, less than ¼, or even less than 10% of the maximum dose advised by the manufacturer for the second active agent when administered without combination administration of a compound of Formula (I).

Methods of use include providing a compound of Formula (I) as a packaged composition. Such method include provided a compound of Formula (I) in a container together with instructions for using the compound to treat a painful disorder or an opioid addiction. The packaged composition may include one or more additional active agents.

Within separate aspects, this disclosure provides a variety of non-pharmaceutical in vitro and in vivo uses for compound of Formula (I). For example, such compounds may be labeled and used as probes for the detection and localization of H3 receptor mu, delta, and/or kappa opioid receptors (in samples such as cell preparations or tissue sections, preparations or fractions thereof).

In addition, compounds provided herein that comprise a suitable reactive group (such as an aryl carbonyl, nitro or azide group) may be used in photoaffinity labeling studies of receptor binding sites. Compounds provided herein may further be used as positive controls in assays for receptor activity, as standards for determining the ability of a candidate agent to bind to an opioid receptor, or as radiotracers for positron emission tomography (PET) imaging or for single photon emission computerized tomography (SPECT). Such methods can be used to characterize opioid receptors in living subjects.

The disclosure provides isotopically and radio labeled compounds of Formula (I). A compound of Formula (I) may be labeled using any of a variety of well-known techniques (e.g., radiolabeled with a radionuclide such as tritium, as described herein), and incubated with a sample for a suitable incubation time (e.g., determined by first assaying a time course of binding).

EXAMPLES

Abbreviations

The following abbreviations are used in the reaction schemes and examples, which follow. This list in not meant to be an all-inclusive list of abbreviations used in the application as additional standard abbreviations, which are readily understood by those skilled in the arts of organic synthesis and pain biology, may also be used in the synthetic schemes and examples.

CPA conditioned place avoidance
CPP conditioned place preference
DAMGO mu opioid receptor selective peptide agoinist, D-Ala-MePhe[4]
DPDPE delta opioid receptor selective peptide agonist, Tyr-D-Pen-Gly-Phe-D-pen, also called [D-Pen[2,5]]Enkephalin
HOAc Acetic Acid
PC place-conditioning
U69593 kappa receptor selective agonist, N-methyl-2-phenyl-N-[(5R,7S,8S)-7-pyrrolidin-1-yl-1-oxaspiro[4.5]decan-8-yl]acetamide, Cas. Reg. No. 96744-75-1

Example 1

Synthesis of Morphinan Compounds with Balanced Receptor Binding Activity

Compound 5, a cyclopropyl-substituted morphinan, is prepared as shown in Scheme A. Levorphanol is esterified with benzoyl chloride and N-demethylated smoothly with an azodicarboxylate ester to produce, after hydrolysis of the intermediate hydrazide, nor-Levorphanol benzoate (compound 1), the starting material for all subsequent analog preparations. Treatment of compound 1 with cyclopropylmethylketone in the presence of $NaCNBH_3$ and acetic acid catalyst results in the N-alkylation desired for intermediates 2a in good yield. Separation of diasteromers by chromatography, selective crystallization, or salt formation with a chiral acid, such as L-tartaric acid, followed by ester removal, completes the synthesis. Compounds 6 and 7 can be similarly prepared using 2-butanone and 2-pentanone as starting materials. The vinyl-analog compounds require an alternative approach, also shown in Scheme A. Compound 1 is condensed with lactonitrile to produce the N-2-propionitrile intermediate (compound 3), which can then be alkylated with vinyl magnesium bromide. The intermediate compound 4, after isomer separation and de-esterification, yields compound 8.

0.01 mole of (−)-nor-levorphanol [3.35 gm] is stirred in 100 mL of methyl cyclopropyl ketone, 12 ml isopropanol, and 22 mk acetic acid at 70° C. Then, a solution of 15 g of sodium cyanoborohydride in 15 m of isopropanol is added in 8 portions over 45 minutes. Reaction mixture was quenched with $H_2O$ and product 2 isolated as colorless gum, weight 3.15 g, 0.0075 mole, 75% yield. Then 3.15 g 2a, a 50:50 mixture of diasteroemers, is dissolved in 25 mL of acetone and treated with 0.5 eq [0.00375 mole] of ditoluoyl-1-tartaric acid, and the salt of the desired diastereomer crystallized in 60% theoretical yield, 1.80 g [0.0022 mole]. Solution of the salt of 2a in MeOH and treatment with sodium hydroxide to remove the ester, affords the 0.62 g of the product 5 in 90% yield

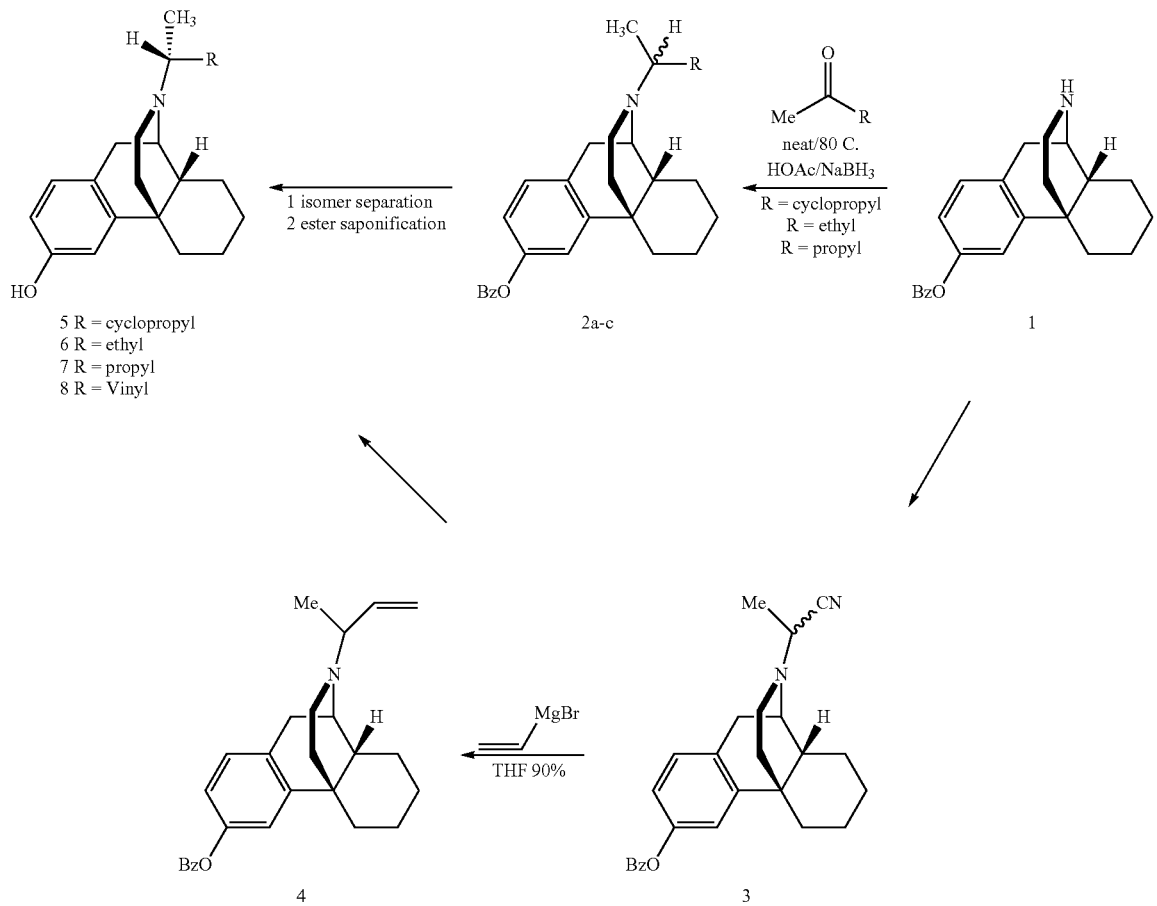

Scheme A

Example 2

In Vitro Assessment of Opioid Receptor Binding Affinity and Functional Affinity Binding affinity and functional activity in [$^{35}$S]GTP γS assays are conducted on membranes derived from CHO cells, developed in our laboratory, that have been transfected with human mu, delta, and kappa receptors, by methods well-known in the literature (Toll L., et al., *NIDA Res. Monograph 178, The College on Problems of Drug Dependence,* 59th Annual Meeting, pp. 440-466. (1998)). Binding studies will be conducted in 1 ml aliquots in a 96-well format for with a 1 hr incubation at 25° C. The incubation will contain [$^3$H] DAMGO (51 Ci/mmol, 1.6 nM), [$^3$H]Cl-DPDPE (42 Ci/mmol, 1.4 nM), [$^3$H]U69593 (41.7 Ci/mmol, 1.9 nM), for mu, delta, and kappa receptors, respectively. Nonspecific binding is determined with 1M of unlabeled DAMGO, DPDPE, and ethylketo-cyclazocine.

Samples are filtered, and radioactivity counted. IC50 values and Hill coefficients are determined using at least six concentrations of each analog and calculated using Graphpad/Prism (ISI, San Diego, Calif.). Ki values are determined by the Cheng and Prusoff method. Compound 5 in Scheme A has been tested in this assay and found to exhibit a Ki of 0.36±0.1 nM (Mu), 2.47±0.1 nM (delta), and 0.29±0.1 nM (kappa).

[$^{35}$S]GTP γS binding studies are conducted as described (Traynor J. R. and Nahorski S. R. *Mol. Pharmacol.* 47: 848-854, (1995), and Toll, L., et al. (1998)). Membranes are prepared as for receptor binding studies using standard methods. Membranes (8-15 g protein) are incubated with [$^{35}$S]GTP γS (50 pM), GDP (10 M), and test compound in 1-ml aliquots for 1 hr at 25 C. Samples are filtered and data analyzed as described above. Compound 5 in Scheme A has been tested in this assay and found to exhibit an EC50 of 4.30±2.1 nM and percent stimulation of 22.6±0.1% at the mu receptor, an EC50 of 9.01±2.6 nM and percent stimulation of 39.8±3.9% at the delta receptor, and EC50 of 2.99±0.9% and percent stimulation of 41.7±5.0 percent at the kappa receptor.

Example 3

Assay for (A) Analgesic Activity, Including Duration of Action, in the Tailflick Assay in Mice, and (B) Potential for Abuse Liability, Using the CPP Assay in Mice The tailflick assay is used to measure antinociceptive activity and the conditioned place preference (CPP) paradigm is used to identify potential abuse liability. CPP has been used to measure rewarding as well as aversive properties of drugs of abuse. The PC (place-conditioning) paradigm measures the incentive motivational properties of stimuli that become associated with drug effects through classical conditioning. The drug is administered in a distinct environment. After several pairings, the environment becomes associated with the effects of the drug, thereby acquiring incentive/motivational properties. Thus, the environment becomes a cue eliciting approach (i.e., conditioned place preference; CPP) if rewarding properties of the drug have been conditioned. The PC (place-conditioning) paradigm offers several advantages. (1) Both rewarding and aversive properties of drugs can be assessed using this procedure. (2) Other behavioral measures, such as locomotor activity, can be assessed following acute as well as repeated drug administration. (3) Nonspecific effects of the drug on motor and sensory systems do not influence the behavioral measure, since animals are tested in a drug-free state. Other advantages of this paradigm over self administration are that the technique is relatively inexpensive, non-invasive, and technically simple to carry out.

Antinociceptive Activity.

Tail-flick latency is determined for each test compound as we have described (79,80) with an analgesia instrument (Stoelting) that uses radiant heat. This instrument is equipped with an automatic device to quantify tail-flick latency and cut off heat after 15 sec to prevent damage to the animal's tail. Following baseline measures, animals receive an subcutaneous injection of their assigned compound (0.1 to 10 mg/kg) and then assessed for tail-flick latencies at 10, 30, 60, 120, and 240 min post-injection.

Anti-nociception (% MPE) is quantified using the following formula:

$$\% MPE = 100 \times [(\text{test latency} - \text{baseline latency})/(15 - \text{baseline latency})].$$

If the animal does not respond before the 15 sec cutoff, it is assigned a score of 100%.

Behavioral results are analyzed using analyses of variance (ANOVA) with drug treatment as the between-group variables and post-drug treatment time as the repeated measure, followed by appropriate one-way ANOVA and Student Newman-Keuls post hoc tests, when appropriate.

Conditioned Place Preference.

Compounds are characterized based upon in vitro activity and antinociceptive activity. Two-day conditioning trials are conducted over eight consecutive days, using a non-biased approach, as described (Khroyan T V, et al., *J. Pharmacol. Exp. Ther.* 320:934-43 (2007) and Toll, L, et al. *J. Pharmacol. Exp. Ther.* 331:954-64 (2009)). Briefly, on one day of the trial, animals are injected with their test compound and confined to one of the conditioning compartments for 20 min. On the next day, they are injected with saline and confined to the other compartment for 20 min. Global activity (measured by the computer) and behavior (measured by the experimenter; see below) are assessed.

Test for Place Conditioning (PC).

24 hr after the last conditioning day, the animals are tested for PC. The solid partition is replaced with a partition containing an opening giving the animal access to both compartments simultaneously for 15 min. The amount of time the animal spends in each compartment is recorded. If the animal spends significantly more time in the drug-paired compartment, this is termed a conditioned place preference (CPP), which is thought to reflect the rewarding properties of a drug.

Statistical Analysis.

For the PC data, the difference in the amount of time spent in the drug-paired compartment minus the saline-paired compartment is calculated. These difference scores are analyzed using an ANOVA, with dose of nicotine and/or TCP as between-subject measures. Fisher LSD tests are additionally used to compare difference scores of each dose to the vehicle control groups. These comparisons are used because ANOVA is not always sensitive enough to detect changes at specific drug doses for two reasons: (1) the effect size of CPP/CPA is typically small, and (2) the graded effects and variability observed with dose-response data often result in non-significant main effects, obscuring potential group differences.

What is claimed is:

1. A compound of the formula

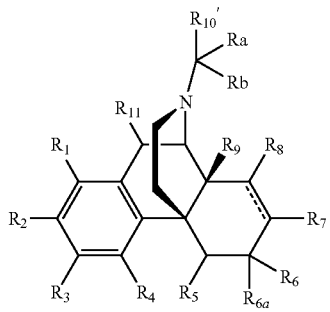

or a pharmaceutically acceptable salt thereof, wherein
$R_1$, $R_2$, $R_4$, $R_5$, $R_6$, $R_{6a}$, $R_7$, $R_8$, $R_9$, and $R_{11}$ are independently selected from hydrogen, halogen, hydroxyl, amino, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy;
$R_{10}'$ is halogen, hydroxyl, amino, $C_1$-$C_4$alkyl, $C_1$-$C_4$alkoxy, mono- or di-$C_1$-$C_4$alkylamino, cyclopropyl, vinyl, $C_1$-$C_2$haloalkyl, or $C_1$-$C_2$haloalkoxy;
$R_3$ is hydroxyl, halogen, or $C_1$-$C_4$alkoxy;
$R_a$ is hydrogen or halogen; and
$R_b$ is halogen, methyl, or ethyl.

2. A compound or salt of claim 1, wherein
$R_1$, $R_2$, $R_4$, $R_5$, $R_6$, $R_6a$, $R_7$, $R_8$, $R_9$, and $R_{11}$ are independently selected from: hydrogen, halogen, $C_1$-$C_2$alkyl, and $C_1$-$C_2$alkoxy.

3. A compound or salt of claim 1, wherein $R_3$ is hydroxyl.

4. A compound or salt of claim 1, wherein
$R_1$, $R_2$, $R_4$, $R_5$, $R_{6a}$, $R_7$, $R_8$, $R_9$, and $R_{11}$ are all hydrogen;
$R_3$ is hydroxyl; and
$R_6$ is hydrogen or hydroxyl.

5. A compound or salt of claim 1 of the formula

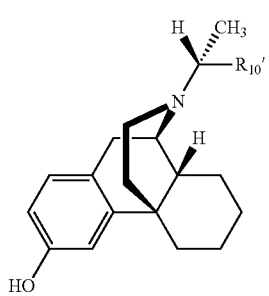

wherein $R_{10}'$ is cyclopropyl, ethyl, propyl, or vinyl.

6. A compound of claim 1, or a salt thereof, wherein the compound is

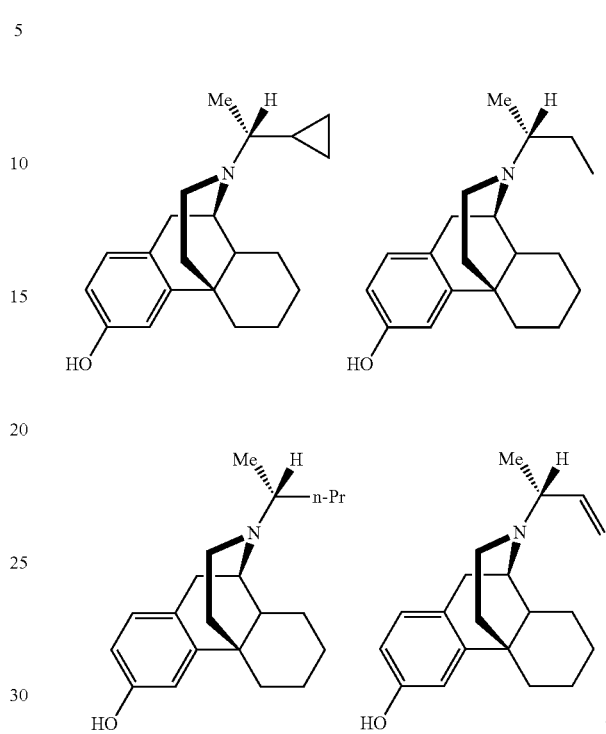

7. A pharmaceutical composition comprising a compound of claim 1, together with a pharmaceutically acceptable carrier.

8. A method of treating pain or opioid addiction comprising administering an effective amount of a compound of claim 1 to a patient in need of such treatment.

9. A method for preparing a compound of claim 1, comprising
isolating one diastereomer from a mixture of diastereomers, where the mixture of diastereomers is prepared by demethylating Levorphanol and N-alkylating the demethylated product.

* * * * *